United States Patent

Schagerström et al.

Patent Number: 5,823,046
Date of Patent: Oct. 20, 1998

[54] MEASURING VESSEL

[76] Inventors: Tonie Schagerström, P.O. Box 442, Uppsala, Sweden, S-754 31; Pär Eriksson, Molngatan 6, Uppsala, Sweden, S-754 31; Anders Olsson, Jakobsbergsgatan 18B, Sala, Sweden, S-733 34

[21] Appl. No.: 896,419

[22] Filed: Jul. 18, 1997

Related U.S. Application Data

[63] Continuation of Ser. No. 605,091, Mar. 6, 1996, abandoned.

[30] Foreign Application Priority Data

Sep. 14, 1993 [SE] Sweden .................................. 9302988

[51] Int. Cl.[6] ..................................................... G01F 19/00
[52] U.S. Cl. ............................................... 73/427; 215/365
[58] Field of Search ....................... 73/426–427; 215/365

[56] References Cited

U.S. PATENT DOCUMENTS

| | | | |
|---|---|---|---|
| 941,489 | 11/1909 | Beverly | 73/427 |
| 1,094,350 | 4/1914 | Walter | 73/427 |
| 1,425,800 | 8/1922 | Small | 73/426 |
| 1,542,777 | 6/1925 | Ladd | 73/426 |
| 1,547,562 | 7/1925 | Byrd | 73/426 |
| 1,678,540 | 7/1928 | Trenner | 73/426 |
| 3,058,352 | 10/1962 | Graham et al. | 73/427 |

FOREIGN PATENT DOCUMENTS

| | | | |
|---|---|---|---|
| 0053693 | 11/1918 | Sweden | 73/427 |
| 121084 | 12/1918 | United Kingdom . | |

*Primary Examiner*—Diego F.F Gutierrez
*Attorney, Agent, or Firm*—Young & Thompson

[57] ABSTRACT

A measuring vessel for measuring finely-ground packable and dry material, such as ground brewing coffee, cocoa, flour and so on is provided which includes a measuring tube (1) which is open at both ends. The bottom end of the tube includes a constriction (3) with an opening which is defined by an edge (4) which slopes relative to the horizontal plane. The measuring vessel is inserted vertically into the finely-ground material and the material enters the vessel from beneath, through the bottom opening. When the vessel is lifted, the material collected in the vessel will remain therein by virtue of frictional bounds in the material, until the vessel is turned upside down, whereupon the material will run out through the top opening.

21 Claims, 1 Drawing Sheet

MEASURING VESSEL

This application is a continuation of application Ser. No. 08/605,091, filed Mar. 6, 1996, now abandoned.

BACKGROUND OF THE INVENTION

1. Field of the Invention

The present invention relates to a measuring vessel or to a measure for measuring finely-ground packable material, such as ground brewing coffee, cocoa, flour, powdered sugar, gruel powder and like packable materials.

2. Description of the Related Art

Conventional measuring vessels for this purpose normally have the form of scoops of varying volumes. When measuring with the aid of scoops, however, certain disadvantages are encountered, which at times are experienced as clear drawbacks to the method:

- Poor measuring accuracy, because the scoop cannot be used to the same level of accuracy each time, wherewith any measuring error is liable to be multiplied by repeating an error with each scooped quantity.
- Spillage, partly caused by material adhering to the outer surface of the scoop and partly because the measured material is able to "run" readily over the edge or lip of the scoop.
- A risk of measurement errors, because counting of the number of scoops that have been taken is disturbed.
- Hand and wrist movements performed in the measuring procedure are uncomfortable for persons who are handicapped in their movements in some way, for instance as the result of wearing a supportive bandage, dressing, etc., and because of pain or because of age, which further increases the risk of spillage from the scoop.

SUMMARY OF THE INVENTION

The drawbacks of the conventional scoop enumerated above can be avoided to great extent by the inventive measuring vessel, the aim of which is to provide an auxiliary device for measuring finely-ground, packable and pourable material and which by virtue of its construction and the method in which it is used facilitates precise measuring of the material concerned, reduces spillage and can be handled comfortably by persons who are handicapped in their movements.

This object of the invention is fulfilled with a measuring vessel according to claim 1.

BRIEF DESCRIPTION OF THE DRAWINGS

The measuring vessel and its method of use will now be described in more detail with reference to the accompanying drawing, in which.

DESCRIPTION OF THE PREFERRED EMBODIMENT(S)

Figure 1:
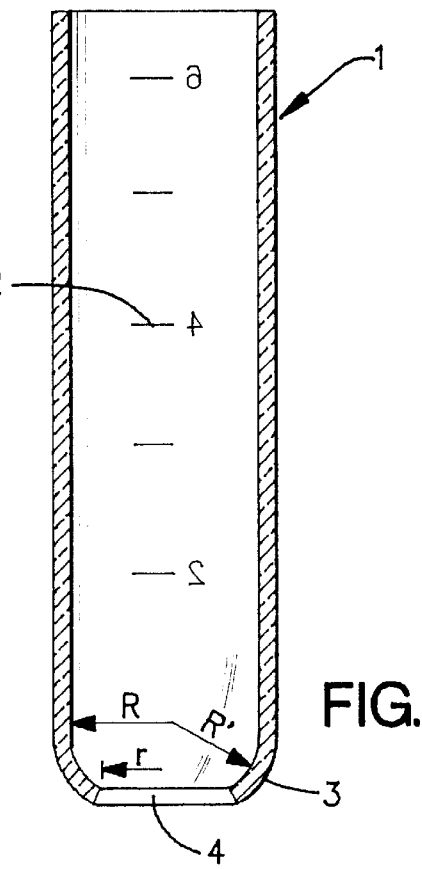
FIG. 1 is an axial cross-sectional view of one preferred embodiment of the measuring vessel.
Figure 4:
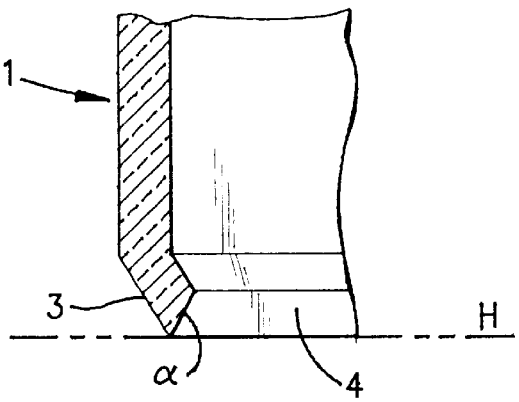
FIG. 4 illustrates an alternative embodiment of one part of the measuring vessel.
Figure 2:
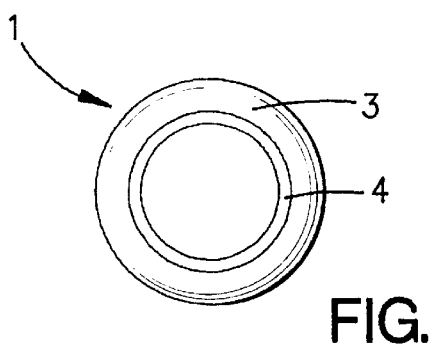
FIG. 2 is an end view of the vessel shown in FIG. 1 from beneath.

According to one preferred embodiment, the measuring vessel is comprised of a tube or hollow cylinder which preferably has a round cross-section along the whole of its length, said tube being generally referenced 1 in FIG. 1. By round is meant here a generally round form which can include both circularly rounded and ovally or elliptically rounded cross-sectional shapes. The measuring vessel 1 is transparent so that the quantity of material taken-up in the vessel can be read against a graduated scale 2 printed on or etched in the outer surface of the measuring vessel, and to this end is preferably made of a hard plastic material, for instance an acrylic material. The measuring vessel 1 is open at both ends and includes at the bottom end of the vessel a constriction 3, which may be spherical, as shown in FIG. 1, or conical as shown in FIG. 4. The constriction 3 can be readily produced by the person skilled in the art of manufacture, by heating and forming. When the constriction 3 has a spherical form, its radius $R'$ may be equal to the internal radius R of the straight cylindrical part of the measuring vessel. To facilitate penetration of the material into the measuring vessel, the constriction 3 includes an opening whose edge 4 is suitably bevelled towards the horizontal plane H at an angle $\alpha$. The angle $\alpha$ may vary and will preferably lie within the range of 45°–65°, preferably 55°–60°.

In the case of a tested, well-functioning and preferred embodiment, the opening defined by the constriction has a radius r which is about three-quarters of the inner radius R of the measuring vessel 1. Experience has shown that this ratio provides a suitable balance between the ability of the measuring vessel to retain material and its resistance and tendancy of packing of the material when pressing the measuring vessel down to collect a measured amount of powdered material in the vessel.

Figure 3:
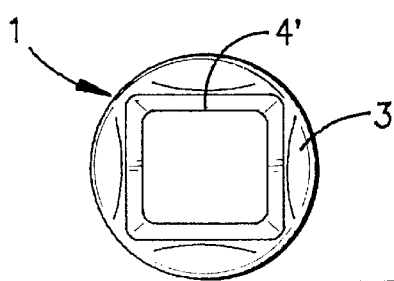
FIG. 3 illustrates an alternative embodiment of the measuring vessel in a view corresponding to the view of FIG. 2.
Figure 6:
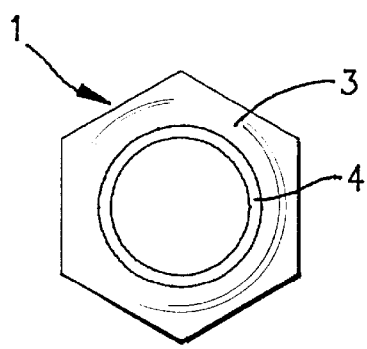
FIG. 6 illustrates an alternative embodiment of the measuring vessel, in a view corresponding to the view of FIG. 2, depicting a polygonal cross section of a measuring tube of the present invention.

The measuring vessel 1 may alternatively have a square or polygonal cross-section (not shown) or a circular cross-section with a square or polygonal bottom opening edge 4' as shown in FIG. 3.

When intended for measuring small quantities of finely-ground material, such as ground brewing coffee or cocoa, the measuring vessel will suitably have an inner diameter of 25–30 mm, while when intended for measuring larger quantities of material, such as flour for instance, may have an inner diameter of up to about 40–45 mm.

The length of the measuring vessel may vary, although as a reference the measuring vessel of one preferred embodiment has a length of about 20 cm with an inner diameter of about 25 mm, which provides an accurate measurement of ground brewing coffee for at least ten cups of normal size.

It will be understood that the measurements, radii and angles recited in the aforegoing are intended as guidelines for the person skilled in this art, and that optimal construction of a measuring vessel for respective products may result in dimensions that differ from those given above.

Figure 5:
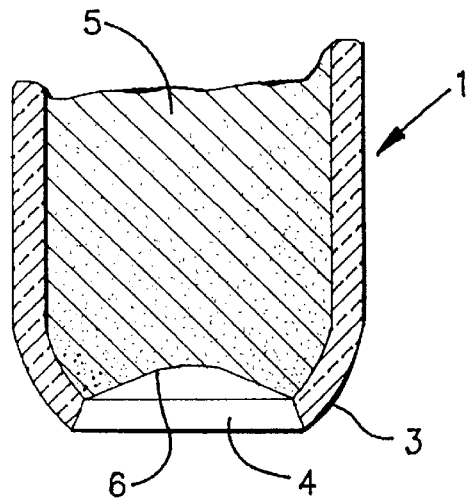
FIG. 5 is a cross-sectional view which illustrates the lower part of the vessel filled with finely-ground material.

The measuring vessel 1 is used to measure a portion of the material concerned by inserting the vessel vertically into the finely-ground material so that the vessel will be filled with a given quantity of said material through the opening in the bottom end of the vessel. When a larger quantity is desired, the measuring vessel is repeatedly pushed down into the finely-ground material, wherewith further material will enter the tube from beneath. When the measuring vessel is lifted out of the finely-ground material, the constriction 3 functions to retain a packed column of material in this region of the vessel and the material is retained within the vessel by the frictional forces acting between the fine particles. As shown in FIG. 5, a characteristic conically concave surface 6 forms on the undersurface of the packed material 5. The volume of this cone corresponds to the amount of material that the vessel is unable to retain when lifted out of the material. If too much material has been collected in the measuring vessel, the excess material can be caused to run out through the opening of the constriction, by knocking the vessel lightly against the wall of the storage container or against the free hand that is not holding the vessel. It has been found, however, that only a very small amount of material will leave the vessel before the characteristic conical bottom surface 6 is recreated and prevents further material from leaving the vessel. This enables the amount of material collected in the measuring vessel to be accurately adjusted in accordance with the graduated scale provided on the vessel.

The measuring vessel is emptied by turning it generally upside down, whereupon the material is able to flow through the upper opening by virtue of the low coefficient of friction of the plastic and the ease with which the powdered material is now able to flow.

It is not necessary to turn the wrist when filling the measuring vessel 1 in accordance with the aforegoing, which makes handling of the measuring vessel easy for those people whose movements are restricted due to supportive bandages or due to rheumatism and so on. Neither will light shaking of the filled vessel cause material to flow therefrom. The risk of erroneous measurements due to a counting error can be avoided in the majority of user situations. The inventive measuring vessel is thus constructed and suitable for use by those user categories which normally find it difficult to handle conventional scoop measures.

We claim:

1. A measuring vessel for measuring finely ground coffee, cocoa powder, flour for baking, gruel and other packable, dry materials with similar properties of being compressible under an externally applied pressure, having the form of a hollow, graduated measuring tube made from transparent material which extends in the direction of a longitudinal axis from a first end to an opposite second end, said measuring tube being open at said first end for introducing a desired volume of said finely ground, packable and dry material by vertically inserting the tube in the material, and open at said second end for dispensing captured material when the measuring tube is inverted from a vertical orientation, said measuring tube having a portion along said longitudinal axis with a uniform cross section, and means at said first end and extending from said portion for retaining a packed column of said finely ground, packable and dry material in said measuring tube in a region of said first end, including when said measuring tube is removed from said material and maintained in a generally vertical direction, until dispensing the captured material through said open second end by inverting the measuring tube.

2. The measuring vessel of claim 1 wherein said retaining means comprises a conical constriction at said first end, said conical constriction having a circular opening, said circular opening having an opening-defining edge which slopes relative to a plane which extends transversely relative to said longitudinal axis.

3. The measuring vessel of claim 2 wherein said opening-defining edge slopes relative to said plane at an angle of about 45°–60°.

4. The measuring vessel of claim 2 wherein said measuring tube is cylindrical and has an internal radius, and further wherein said circular opening has a radius approximately corresponding to three-quarters of said internal radius.

5. The measuring vessel of claim 1 wherein said retaining means comprises a conical constriction at said first end, said conical constriction having a polygonal opening, said polygonal opening having an opening-defining edge which slopes relative to a plane which extends transversely relative to said longitudinal axis.

6. The measuring vessel of claim 5 wherein said opening-defining edge slopes relative to said plane at an angle of about 45°–60°.

7. The measuring vessel of claim 1 wherein said retaining means comprises a spherical constriction at said first end, said spherical constriction having a circular opening, said circular opening having an opening-defining edge which slopes relative to a plane which extends transversely relative to said longitudinal axis.

8. The measuring vessel of claim 7 wherein said opening-defining edge slopes relative to said plane at an angle of about 45°–60°.

9. The measuring vessel of claim 7 wherein said measuring tube is cylindrical and has an internal radius, and further wherein said spherical constriction has a radius which is equal to said internal radius.

10. The measuring vessel of claim 7 wherein said measuring tube is cylindrical and has an internal radius, and further wherein said circular opening has a radius approximately corresponding to three-quarters of said internal radius.

11. The measuring vessel of claim 1 wherein said retaining means comprises a spherical constriction at said first end, said spherical constriction having a polygonal opening, said polygonal opening having an opening-defining edge which slopes relative to a plane which extends transversely relative to said longitudinal axis.

12. The measuring vessel of claim 11 wherein said opening-defining edge slopes relative to said plane at an angle of about 45°–60°.

13. The measuring vessel of claim 11 wherein said measuring tube is cylindrical and has an internal radius, and further wherein said spherical constriction has a radius which is equal to said internal radius.

14. A measuring vessel for use with finely ground packable, dry material, comprising:

a tube extending in the direction of a longitudinal axis from a first end to a second end, said first end and said second end consisting essentially of a respective first opening and second opening, said first opening and said second opening being free of any closure, said tube having a portion along said longitudinal axis with a uniform cross section;

means at said first end and extending from said portion for (a) filling said tube with finely ground packable, dry material at said first end by inserting said tube in a generally vertical direction into said material so that said material enters said tube at said first opening; (b) retaining said material in said tube when said tube is removed from said material and maintained in said generally vertical direction; (c) adjusting for a measured amount of said material in said tube by removing from said tube, while holding said tube in said generally vertical direction, any amount of said material in excess of said measured amount by tapping said tube against an object sufficiently to remove said excess from said tube at said first opening and retain said measured amount in said tube; and (d) emptying said tube by inverting said tube and dispensing said material at said second opening.

15. The measuring vessel of claim 14 wherein said means comprises a conical constriction at said first end, said conical constriction having a circular opening, said circular opening having an opening-defining edge which slopes relative to a plane which extends transversely relative to said longitudinal axis.

16. The measuring vessel of claim 14 wherein said means comprises a conical constriction at said first end, said conical constriction having a polygonal opening, said polygonal opening having an opening-defining edge which slopes relative to a plane which extends transversely relative to said longitudinal axis.

17. The measuring vessel of claim 14 wherein said means comprises a spherical constriction at said first end, said spherical constriction having a circular opening, said circular opening having an opening-defining edge which slopes relative to a plane which extends transversely relative to said longitudinal axis.

18. The measuring vessel of claim 14 wherein said means comprises a spherical constriction at said first end, said spherical constriction having a polygonal opening, said polygonal opening having an opening-defining edge which slopes relative to a plane which extends transversely relative to said longitudinal axis.

19. The measuring vessel of claim 14 wherein said uniform cross section is circular.

20. The measuring vessel of claim 14 wherein said uniform cross section is polygonal.

21. In a measuring vessel for use with finely ground packable, dry material, said measuring vessel being made from transparent material, extending in the direction of a longitudinal axis from a first open end to an opposite second open end, and including a bore which extends in said direction from said first open end to said second open end, said first open end and said opposite second open end being free of any closure, wherein the improvement comprises, a hollow, graduated measuring portion along said longitudinal axis having a uniform cross section which extends in said direction from said first open end towards said opposite second open end, said graduated measuring portion having a tubular configuration and including a first length of said bore; and a constriction portion which extends from said measuring portion in said direction from said second open end towards said first open end, said constriction portion including a second length of said bore, said constriction portion being structured and arranged to retain finely ground, packable, dry material in said bore when said vessel is removed from said material and maintained in a generally vertical direction, said constriction portion having a spherical configuration.

* * * * *